United States Patent [19]

Khouri et al.

[11] Patent Number: 5,067,963
[45] Date of Patent: Nov. 26, 1991

[54] METHOD OF MAKING LIVE AUTOGENOUS SKELETAL REPLACEMENT PARTS

[75] Inventors: Roger K. Khouri, St. Louis, Mo.; A. Harri Reddi, Bethesda, Md.

[73] Assignee: Washington University, St. Louis, Mo.

[21] Appl. No.: 570,442

[22] Filed: Aug. 21, 1990

[51] Int. Cl.$^5$ .......................... A61F 2/28; A61F 2/36
[52] U.S. Cl. .................................. 623/16; 623/10; 623/11; 623/18; 623/23; 623/901
[58] Field of Search ................ 623/901, 10, 11, 16–23

[56] References Cited

U.S. PATENT DOCUMENTS

| | | | |
|---|---|---|---|
| 4,294,753 | 10/1981 | Urist | 260/112 R |
| 4,430,760 | 2/1984 | Smestad | 623/10 |
| 4,434,094 | 2/1984 | Seyedin et al. | 623/11 X |
| 4,440,750 | 4/1984 | Glowacki et al. | 424/95 |
| 4,455,256 | 6/1984 | Urist | 260/112 R |
| 4,485,097 | 11/1984 | Bell | 424/95 |
| 4,526,909 | 7/1985 | Urist | 523/115 |
| 4,563,489 | 1/1986 | Urist | 524/21 |
| 4,619,989 | 10/1986 | Urist | 530/417 |
| 4,620,327 | 11/1986 | Caplan et al. | 623/10 |
| 4,761,471 | 8/1988 | Urist | 530/350 |
| 4,774,228 | 9/1988 | Seyedin et al. | 623/11 X |
| 4,789,932 | 12/1988 | Urist | 530/350 |
| 4,795,804 | 1/1989 | Urist | 530/350 |
| 4,857,456 | 8/1989 | Urist | 435/7 |
| 4,992,226 | 2/1991 | Piez et al. | 623/901 X |

OTHER PUBLICATIONS

Harakas, Clin. Orthopedics & Rel. Res. No. 188, 239–251 (Sep. 1984).
Wozney et al., Science 242, 1528–1534 (1988).
Urist et al., Science 220, 680–686 (1984).
Sampath and Reddi, Proc. Natl. Acad. Sci. U.S.A. 80, 6591–6595 (1983).
Sampath et al., Proc. Natl. Acad. Sci. U.S.A. 84, 7109–7113 (1987).
Luyten et al., J. Biol. Chem. 264, 13377–13380 (1989).
Reddi et al., Proc. Natl. Acad. Sci. U.S.A. 69, 1601–1605 (1972).
Reddi et al., Proc. Natl. Acad. Sci. U.S.A. 71, 1648–1652 (1974).
Reddi et al., Proc. Natl. Acad. Sci. U.S.A. 74, 5589–5592 (1971).

Primary Examiner—Robert A. Hafer
Assistant Examiner—Kevin G. Rooney
Attorney, Agent, or Firm—Scott J. Meyer; James W. Williams, Jr.

[57] ABSTRACT

A novel method is disclosed for the manufacture of live autogenous skeletal replacement parts through muscle flap molding and osteoinduction comprising the steps of:

a) forming a mold of physiologically inert support material into the shape of a replacement part for a defective skeletal site,
b) placing a muscle flap into the cavity of the mold,
c) thoroughly incorporating osteoinductive factor in the muscle flap,
d) closing the mold,
e) allowing osteogenesis to take place, and
f) implanting the resulting newly formed bone into the defective skeletal site.

7 Claims, 4 Drawing Sheets

METHOD OF MAKING LIVE AUTOGENOUS SKELETAL REPLACEMENT PARTS

BACKGROUND OF THE INVENTION

This invention relates to a method of making live autogenous skeletal replacement parts. More particularly, the present invention is concerned with the manufacture of live autogenous skeletal replacement parts through muscle flap molding and osteoinduction.

Bony defects, whether from degenerative, traumatic or cancerous etiologies, pose a formidable challenge to the reconstructive surgeon. Although many types of bone grafts and numerous biocompatible materials have been used clinically, they all suffer from shortcomings or potential long term complications. See, for example, Urist, "Bone transplants and implants" in *Fundamental and Clinical Bone Physiology*, Chapter 11, Lippincott, Philadelphia, Pa., 1980, pp. 331–368; Habal and Reddi, "An update on bone grafting and bone substitutes in reconstructive surgery" in *Advances in Plastic and Reconstructive Surgery*, Year Book Medical Publishers, Chicago, Ill., 1987, pp. 147–209.

The search for an off-the-shelf substitute for the conventional autogenous cancellous bone grafts used in orthopedic and maxillofacial surgery has led to considerable research efforts spent towards the isolation and manufacture of osteoinductive factors, e.g., demineralized bone matrix (DBM) and bone morphogenetic protein (BMP) [Urist et al., "Bone Cell Differentiation and Growth Factors," *Science* 220, 680–686 (1984), and Reddi et al., "Biologic Principles of Bone Induction," *Orthop. Clin. of North Am.* 18, 207 (1987)].

Current experimental therapeutic approaches with osteoinduction consist of administering the osteoinductive factors locally at the site of bone deficiency with the expectation that bony transformation of the adjacent tissues around the defect will reconstitute the missing bone [Urist and Dawson, "Intertransverse Process Fusion with the Aid of Chemostrelized Autolyzed Antigen Extracted Allogenic (AAA) Bone," *Clin. Orthop. Relat. Res.* 154, 97 (1981); Hollinger et al., "Calvarial Bone Regeneration Using Osteogenin," *J. Oral Maxillofac. Surg.* 47, 1182 (1989); and Mulliken et al., "Induced Osteogenesis-the Biological Principle and Clinical Applications," *J. Sur. Res.* 37, 487 (1984)]. This obvious and simple clinical application of osteoinduction can only achieve limited popularity for the following reasons:

First, in most clinical situations, and by the nature of the original problem itself, bone defects are associated with adjacent soft tissue deficiencies. The remaining surrounding tissues are usually either atrophic, or densely scarred from trauma, inflammation, infection, or radiation; factors that markedly reduce their osteoinductive potential. With poor responsiveness in addition to tissue deficiency, the amount of bone formed is suboptimal for functional skeletal reconstructions.

Second, osteoinductive factors applied freely within the defect site can cause an indiscriminate bony transformation of the few remaining functional muscles. Furthermore, the many vital structures in the area such as nerves, tendons and ligaments are also subject to ossification. The result can reproduce the dreadful pathologic condition known as myositis ossificans, which causes total loss of function in the affected part of the body.

Third, without any architectural constraints, the simple application of osteoinductive factors at the defect site cannot be expected to result in a piece of bone with the exact three dimensional shape necessary to reconstruct complex skeletal defects such as femoral heads, mandibles, carpal bones, etc.

Further background information on demineralized bone matrix-induced osteogenesis and bone morphogenetic protein (BMP) can be had by reference to the review paper by Harakas, "Demineralized Bone-Matrix-Induced Osteogenesis" in *Clin. Orthopaedics and Related Res.* No. 188, September 1984, pp. 239–251; the research article by Wozney et al., "Novel Regulators of Bone Formation: Molecular Clones and Activities," *Science* 242, 1528–1534 (1988); and U.S. Pat. Nos. 4,294,753; 4,440,750; 4,455,256; 4,485,097; 4,526,489; 4,563,489; 4,619,989; 4,761,471; 4,789,732; 4,795,804; and 4,857,456.

BRIEF DESCRIPTION OF THE INVENTION

In accordance with the present invention a novel method is provided for the manufacture of live autogenous skeletal replacement parts through muscle flap molding and osteoinduction. The method comprises the steps of:

a) forming a mold of physiologically inert support material into the shape of a replacement part for a defective skeletal site, b) placing a muscle flap into the cavity of the mold, c) thoroughly incorporating osteoinductive factor in the muscle flap, d) closing the mold, e) allowing osteogenesis to take place, and f) implanting the resulting newly formed bone into said defective skeletal site.

The method thus employs the threefold combination of muscle flap transfer, soft tissue molding and osteoinduction. These three aspects utilized by the invention are briefly described as follows:

Muscle Flap Transfer

First described by Tansini in 1896, and with currently well over 100 clinically useful muscle flaps described, muscle flap transfer is the workhorse of reconstructive surgery, [Mathes and Eshima, in *McCarthy's Plastic Surgery*, Vol. 1, *General Principles*, W. B. Saunders Co., Philadelphia, 1990, pp. 379–341]. Any muscle or portion of a muscle in the body can be dissected and transferred to a distant site as a muscle flap, where it will maintain its viability and heal, provided its vascular perfusion is preserved or is reconnected at the recipient site via vascular anastomoses. Muscle flap transfer has proven itself clinically as an easy and reliable way to cover complex wounds and has provided a satisfactory solution to the reconstruction of various soft tissue defects. Because muscles function in concert with adjacent agonists, the donor site morbidity associated with the transfer of one muscle from a group is minimal as the function is usually well compensated by the remaining muscles.

Soft Tissue Molding

Fisher in 1987 [Fisher and Yang, *Plast. Reconstr. Surg.* 82, 857 (1988)], described an experimental method for soft tissue molding. Flaps of omental fat were placed in silicone rubber molds of various shapes. Upon removal from the molds one month later, the flap had espoused the shape of the mold. However, since no tissue transformation had occurred, when left outside the molds, the acquired shape of the fatty tissue flaps was rapidly lost. Although he used omental fat flaps, the same principle of soft tissue molding can be extended to muscle flaps.

Osteoinduction

Urist in 1965 [Urist, *Science* 150, 893–899 (1965)], and Reddi in 1972 [Reddi et al, *Proc. Natl. Acad. Sci. USA* 69, 1601–1605 (1972)], have shown that the subcutaneous implantation of demineralized bone matrix (DBM), results in local bone differentiation. A number of polypeptide growth factors with osteoinductive properties have since been derived from DBM. One of these, osteogenin, a 30–40 kDa glycoprotein isolated and sequenced by Reddi et al [Sampath et al., *Proc. Natl. Acad. Sci. USA* 84, 7109–7113 (1987), and Luyten et al., *J. Biol. Chem.* 264, 13377–13380 (1989)] has the capacity to induce the differentiation of mesenchymal tissues into bone. DBM and osteogenin have a synergistic effect as described by Muthukumaran and Reddi, *Collagen Rel. Res.* 8, 433–441 (1988).

Thus, by the method of the invention, a conventional and readily available muscle flap is molded in a general manner as shown by Fisher and Yang, *Plast Reconstr. Surg.* 82, 857 (1988), and under the effect of osteoinductive factors, transformed into a vascularized bone graft of the exact shape and size of the mold.

The osteoinductive factor can be, for example, any of the known bone morphogenetic proteins (BMP), but preferably is the osteogenin used in the illustrative examples hereinafter and described by Sampath et al., supra, and Luyten et al., supra, having a 30–40 kDa molecular weight as determined by SDS-PAGE under non-reducing conditions.

In a preferred embodiment, the inner surface of the mold is coated with demineralized bone matrix (DMB) before placement of the muscle flap into the mold cavity.

The method of the invention essentially satisfies the following five criteria of a preferred grafting material:

1. It is autogenous. By originating from the patient the graft does not become subject to immune rejection.

2. It consists of live vascularized tissue. Live vascularized bone grafts that preserve an intact microcirculation and perfusion through their transfer to the recipient sites, heal in a fashion similar to that of simple fractures. Most importantly, they become incorporated, maintain their shape and do not undergo resorption, regardless of the conditions present at the recipient site [Weiland et al., *Clin. Orthop.* 174, 87 (1983)].

3. It is capable of being precisely contoured to exactly match any defect, whichever complex skeletal shape it is meant to replace.

4. It has virtually unlimited supply and is relatively easy to obtain.

5. It has minimal donor site morbidity.

The fabrication of vascularized live bone grafts through the bony transformation of readily available autogenous muscle flaps is achieved by the method of the invention. Any muscle flap, whether a local muscle transfer, or a distant free muscle flap, can be molded to the desired shape, transformed into bone, and transferred to a defect site, as a prefabricated part. A virtually unlimited supply of donor tissue can thus be made available for the reconstruction of any skeletal defect.

The combination of distant muscle flap transfer and of tissue molding as described herein is a most effective and safe method to therapeutically apply an osteoinductive factor. With the ability to de-novo manufacture vascularized bone grafts of exactly desired shapes and sizes, as custom-made bony spare parts, and to transfer them based on preselected large vascular pedicles, in accordance with the method of the invention, reconstructive capabilities can be significantly expanded and can render obsolete many of the currently used skeletal reconstruction methods.

DETAILED DESCRIPTION OF THE INVENTION

While the specification concludes with claims particularly pointing out and specifically claiming the subject matter which is regarded as forming the present invention, it is believe that the invention will be better understood from the following detailed description of preferred embodiments taken in conjunction with the accompanying drawings in which:

FIGURES

In order to illustrate the invention in greater detail, the following illustrative reconstructive surgery was carried out. It will be appreciated that the invention is not limited to this exemplary work or the specific details set forth in these examples.

EXAMPLES

Materials and Methods

Figure 1:
FIG. 1 shows the thigh adductor muscle flap pedicled upon the ipsilateral femoral vessels which is dissected off the hindleg of the rat.
Figure 2:
FIG. 2 shows molds of various skeletal parts which are casted using inert silicone rubber, and are bivalved open to allow placement of the muscle flaps.
Figure 3:
FIG. 3 shows the muscle flap placed inside the mold along with the osteoinductive factors, and the mold implanted in the subcutaneous pocket. Note that the flap, though secured inside the mold, is still perfused by the femoral vessels pedicle.

In 23 Lewis rats weighing 125–150 grams, thigh adductor muscle flaps pedicled upon the femoral vessels were dissected off the ipsilateral leg as described by Khouri et al., *Surg. Forum* 39, 597 (1988) (FIG. 1). The flaps were placed inside bivalved silicone rubber molds of various shapes (mandible, femoral head, ear skeletal framework, tube, etc.) (FIG. 2). In 18 animals, the flaps were injected with 20 μl of osteogenin (0.2 μg) and the molds were coated with 25 mg of DBM. The dose of osteoinductive factors used is that which is capable of producing total transformation of 750–1000 mg of muscle tissue. The remaining five flaps served as controls, they were injected with 20 μl of the vehicle, and the molds were not coated. The molds, completely filled with the well perfused flaps, were closed and implanted in a subpannicular lower abdominal wall pocket (FIG. 3). Ten days later, the molds were removed and their contents were again isolated as islands flaps. They were examined grossly for their ability to espouse the shape of the mold and histologically for the presence of bone.

RESULTS

Figure 4:
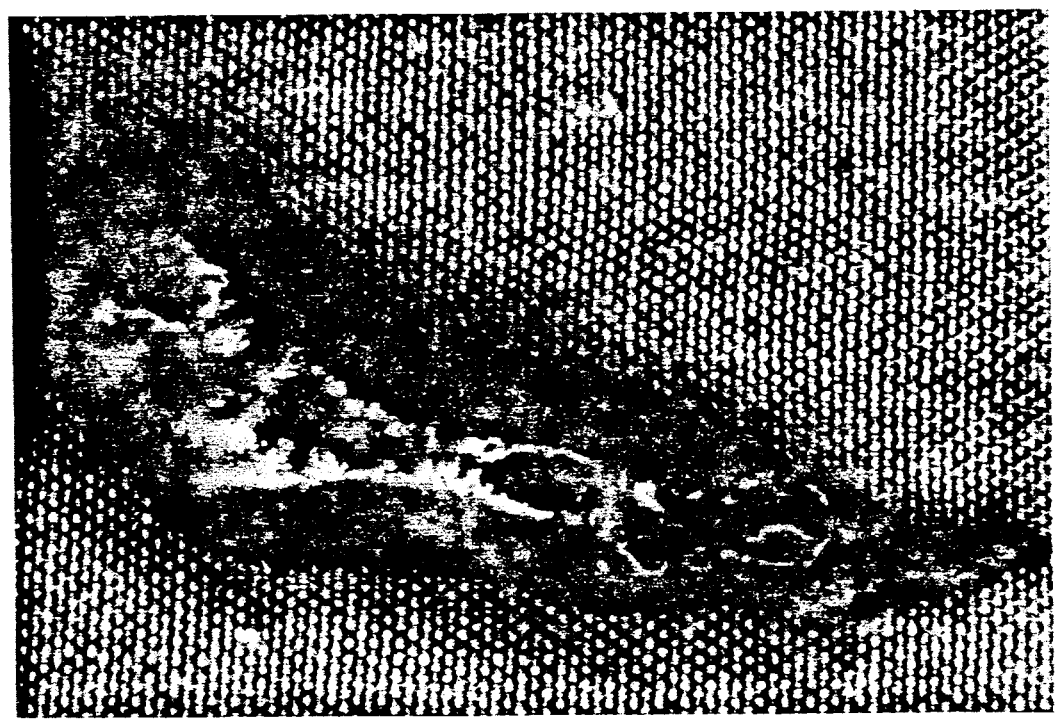
FIG. 4 shows the resultant bony femoral head obtained following removal of the mold 10 days later. Note the femoral vessel pedicle at the inferior portion of the flap.
Figure 5:
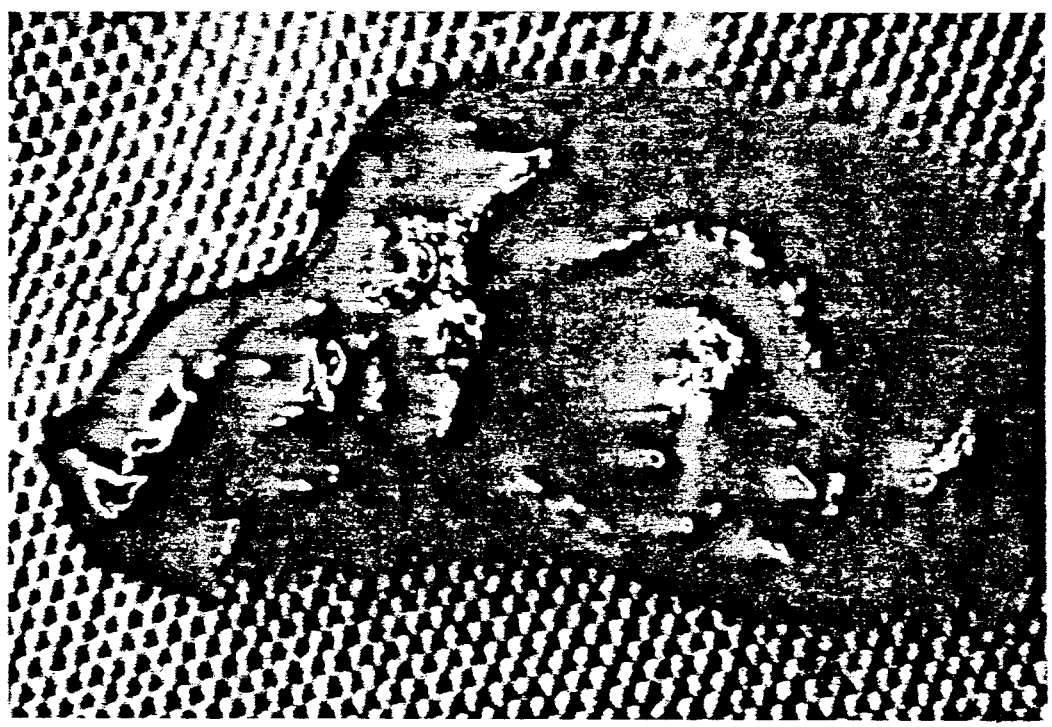
FIG. 5 shows the resultant ear skeletal framework obtained 10 days later. Note the preservation of the delicate contour details.

All of flaps molded in the presence of osteogenin had a rigid, gritty bony appearance and consistency and retained the fine contour details of the molds (FIGS. 4 and 5). In contrast, control flaps were soft and essentially shapeless when they were removed from the molds.

Figure 6:
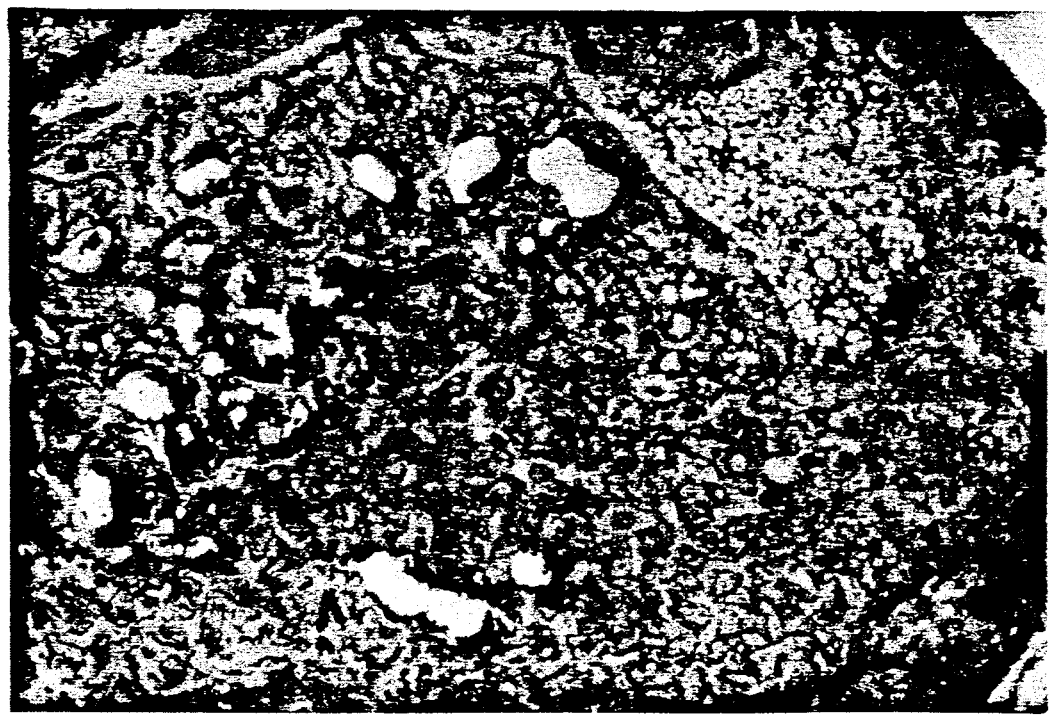
FIG. 6 is a hisotological low power photomicrograph showing complete transformation of the muscle flap into bone tissue 10 days later. (Toluidine blue, 40×)
Figure 7:
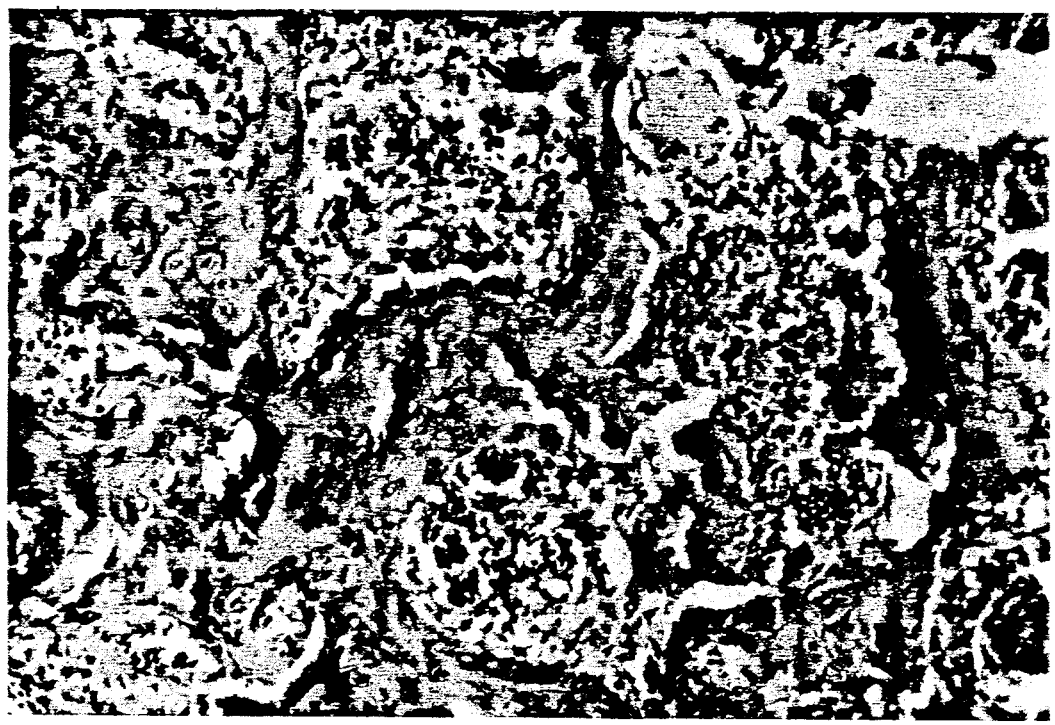
FIG. 7 is a histological detail of the newly formed bone. Note the presence of osteocytes, osteoblasts, osteoclast, and active bone marrow spaces between the calcified bone lamellae. (H&E, 400×)

Histological analysis confirmed that in each instance essentially all of the muscle flap had been transformed into bone. In some areas, the bone had organized into compact lamellae with a central core of bone marrow (FIG. 6). There was no evidence of any bony transformation in any of the control flaps.

Various other examples will be apparent to the person skilled in the art after reading the present disclosure without departing from the spirit and scope of the invention. It is to be understood that all such other examples are included within the scope of the appended claims.

What is claimed:

1. A method for the manufacture of live autogenous skeletal replacement parts through muscle flap molding and osteoinduction comprising the steps of:
   a) forming a mold of physiologically inert support material into the shape of a replacement part for a defective skeletal site,
   b) placing a muscle flap into the cavity of the mold,
   c) thoroughly incorporating osteoinductive factor in the muscle flap,
   d) closing the mold,
   e) allowing osteogenesis to take place, and
   f) implanting the resulting newly formed bone into said defective skeletal site.

2. The method of claim 1 in which the osteoinductive factor is osteogenin of 30–40 kDa molecular weight as determined by SDS-PAGE under non-reducing conditions.

3. The method of claim 1 in which the mold is formed of a silicone rubber material.

4. The method of claim 1 in which the muscle flap is perfused with about 0.2 $\mu$g of osteogenin for each 750–1000 mg of muscle flap tissue.

5. The method of claim 1 in which the inner surface of the mold is coated with demineralized bone matrix before placing the muscle flap into the cavity of the mold.

6. The method of claim 5 in which the mold is coated with about 25 mg of demineralized bone matrix for each 750–1000 mg of muscle flap tissue.

7. A method for the manufacture of live autogenous skeletal replacement parts through muscle flap molding and osteoinduction comprising the steps of:
   a) forming a mold of silicone rubber into the shape of a replacement part for a defective skeletal site,
   b) coating the inner surface of the mold with about 25 mg of demineralized bone matrix for each 750–1000 mg of muscle flap tissue used in the next step,
   c) placing a muscle flap into the cavity of the mold,
   d) thoroughly incorporating in the muscle flap about 0.2 $\mu$g of osteogenin having a molecular weight of about 30–40 kDa as determined by SDS-PAGE under non-reducing conditions for each 750–1000 mg of muscle flap tissue,
   e) closing the mold,
   f) allowing osteogenesis to take place, and
   g) implanting the resulting newly formed bone into said defective skeletal site.

* * * * *